United States Patent
Bhalla

(10) Patent No.: US 8,533,868 B2
(45) Date of Patent: *Sep. 17, 2013

(54) STERILE GLOVE WITH TOUCHLESS DONNING

(76) Inventor: Jagmohan Bhalla, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/226,941

(22) Filed: Sep. 7, 2011

(65) Prior Publication Data

US 2012/0117711 A1  May 17, 2012

Related U.S. Application Data

(63) Continuation of application No. 12/946,554, filed on Nov. 15, 2010, now Pat. No. 8,015,622.

(51) Int. Cl.
A41D 19/00 (2006.01)

(52) U.S. Cl.
USPC ............................. 2/161.7; 2/160

(58) Field of Classification Search
USPC .............. 2/16, 17, 158, 159, 160, 161.7, 901, 2/20, 161.6, 162, 910, 917; 128/856, 878, 128/879; 604/292; 223/111, 112; 602/21; 206/569, 570, 438, 210, 278, 484; 53/425, 53/457; 224/933; D3/329
See application file for complete search history.

(56) References Cited

U.S. PATENT DOCUMENTS

| | | | |
|---|---|---|---|
| 2,041,254 A | 2/1935 | Lipshutz | |
| 2,325,482 A | 9/1941 | Curran | |
| 2,915,173 A * | 12/1959 | Langdon | 206/295 |
| 2,976,540 A | 3/1961 | Sutherland | |
| 4,002,276 A | 1/1977 | Poncy et al. | |
| 4,069,913 A | 1/1978 | Harrigan | |
| 4,155,494 A | 5/1979 | Poncy et al. | |
| 4,159,069 A | 6/1979 | Poncy et al. | |
| 4,845,780 A | 7/1989 | Reimers et al. | |
| 4,868,927 A | 9/1989 | Bourdeau et al. | |
| 4,876,747 A | 10/1989 | Coffey et al. | |
| 4,884,300 A | 12/1989 | Vistins | |
| 4,898,309 A | 2/1990 | Fischer | |
| 4,915,226 A | 4/1990 | Keenan | |
| 4,971,233 A | 11/1990 | Keenan | |
| 5,020,159 A | 6/1991 | Hellickson | |
| 5,020,160 A | 6/1991 | Cano | |
| 5,065,863 A * | 11/1991 | Moyet-Ortiz | 206/210 |
| 5,365,608 A | 11/1994 | Flick | |
| 5,398,344 A | 3/1995 | Hirano | |
| 5,467,483 A | 11/1995 | Saadatmanesh et al. | |
| 5,816,440 A | 10/1998 | Shields et al. | |
| 5,864,883 A | 2/1999 | Reo | |
| 5,864,885 A | 2/1999 | Grinberg | |
| 6,061,833 A | 5/2000 | Smith et al. | |
| 6,375,034 B1 | 4/2002 | Corbett | |

(Continued)

*Primary Examiner* — Amber Anderson

(74) *Attorney, Agent, or Firm* — Miles & Stockbridge, P.C.

(57) ABSTRACT

A sterile glove that includes a hand and finger portion, a cuff having an inside surface and an outside surface, and a cuff rim. The cuff is adapted to be folded over at a fold when the glove is packaged, and a portion of the inside surface of the cuff becomes an outer facing surface when it is folded over. The glove further includes a detachable tab that is coupled to the inside surface and includes a free end and a non-free end. The glove further includes a detachable shield covering at least a portion of the outer facing surface when the cuff is folded over at the fold.

20 Claims, 5 Drawing Sheets

(56) References Cited

U.S. PATENT DOCUMENTS

| | | |
|---|---|---|
| 6,435,388 B1 | 8/2002 | Binder et al. |
| 6,442,761 B1 | 9/2002 | Huang |
| 6,832,708 B2 | 12/2004 | Sinai |
| 7,051,378 B1 | 5/2006 | Mire |
| 7,246,382 B2 | 7/2007 | Plut et al. |
| 7,527,181 B1 | 5/2009 | Sullivan |
| 7,624,455 B1 | 12/2009 | Bhalla |
| 7,665,150 B2 | 2/2010 | Holley |
| 2005/0241046 A1 | 11/2005 | Griesbach et al. |
| 2006/0185059 A1 | 8/2006 | Taha et al. |
| 2007/0061942 A1 | 3/2007 | Schrodl |
| 2008/0172767 A1 | 7/2008 | Friedstrom |
| 2010/0037365 A1 | 2/2010 | Bhalla |

* cited by examiner

US 8,533,868 B2

STERILE GLOVE WITH TOUCHLESS DONNING

RELATED APPLICATIONS

This application is a continuation of U.S. application Ser. No. 12/946,554, filed Nov. 15, 2010, which is herein incorporated by reference.

FIELD OF THE INVENTION

One embodiment is directed generally to a sterile glove, and in particular to a sterile glove that allows for touchless donning.

BACKGROUND INFORMATION

Sterile elastomeric gloves are used with increasing frequency by medical and laboratory professionals to prevent the tactile transfer of foreign materials during various procedures. Sterile gloves are typically packaged with their cuffs folded over to expose a portion of the inner surface of the cuff. This allows the gloves to be picked up and held during donning by touching only the area close to the fold and at some distance from the cuff rim, which minimizes the risk of contamination.

Various structure, packaging and dispenser improvements and techniques have been introduced to address the problems of sterile glove donning. However, these known methods tend to unnecessarily increase the cost and complexity of use and manufacture of the gloves.

SUMMARY OF THE INVENTION

One embodiment is a sterile glove that includes a hand and finger portion, a cuff having an inside surface and an outside surface, and a cuff rim. The cuff is adapted to be folded over at a fold when the glove is packaged, and a portion of the inside surface of the cuff becomes an outer facing surface when it is folded over. The glove further includes a detachable tab that is coupled to the inside surface and includes a free end and a non-free end. The glove further includes a detachable shield covering at least a portion of the outer facing surface when the cuff is folded over at the fold.

DETAILED DESCRIPTION

One embodiment is a sterile glove with a detachable tab and a detachable shield that allows the glove to be donned easily and reliably without touching any of the wearable portion of the glove.

Figure 1:
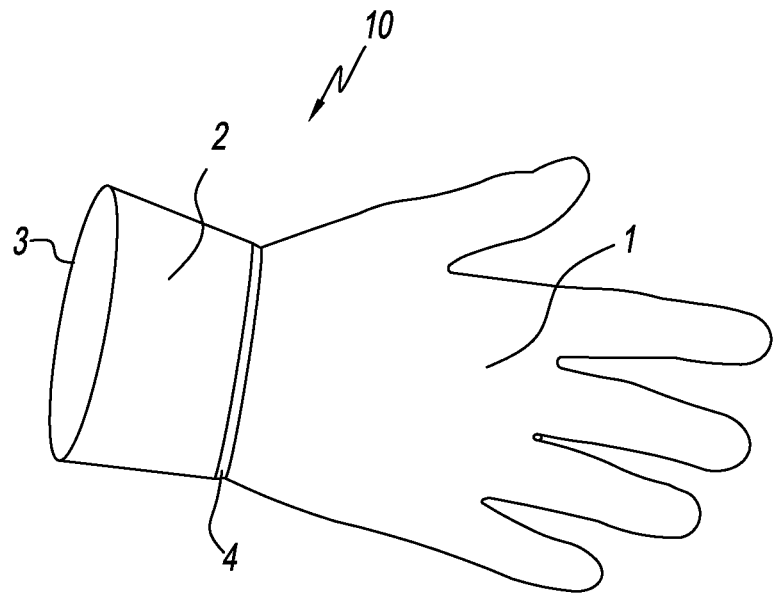
FIG. 1 is a perspective view of a prior art sterile glove as it is configured when it is removed from packaging and before being donned by a user.

FIG. 1 is a perspective view of a prior art sterile glove 10 as it is configured when it is removed from packaging and before being donned by a user. Glove 10 includes a cuff 2, a cuff rim 4, and a finger and hand portion 1. Cuff 2 of glove 10 as shown in FIG. 1 is in a state of being folded over at a fold 3 so that at least some of the inside surface is exposed as an "outer facing surface". This allows glove 10 to be held by touching only the region of the folded over cuff 2 that is near fold 3 thereby limiting contact to an area at some distance from cuff rim 4 and reducing the risk of contamination. The folded over cuff is unfolded before use of the glove. Use of the glove can include any activity after the glove has been donned. "Donning" includes all activities involved in inserting a hand into the glove and in unfolding its cuff.

Figure 2:
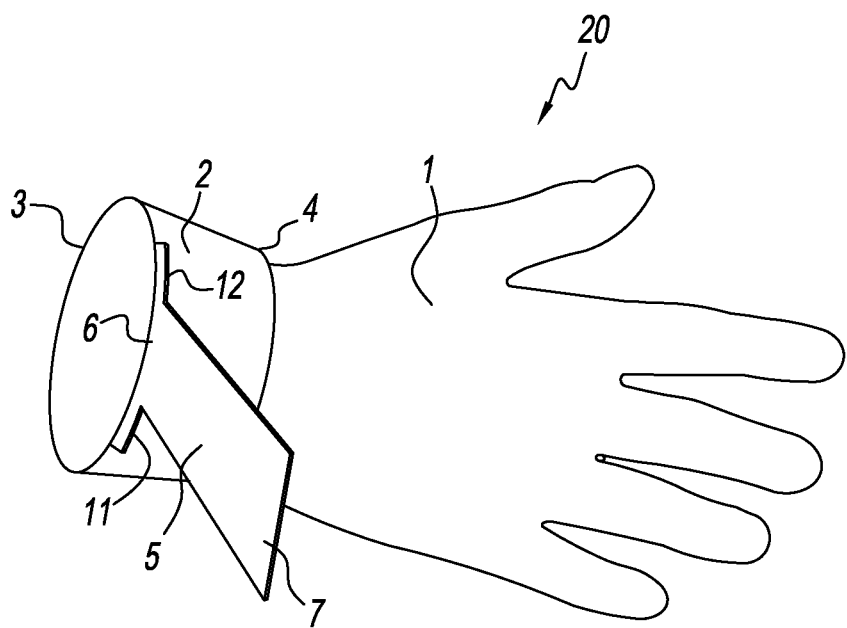
FIG. 2 is a perspective view of a sterile glove in accordance with one embodiment as it is configured when it is removed from its packaging or other storage means and before being donned by a user.

FIG. 2 is a perspective view of a sterile glove 20 in accordance with one embodiment as it is configured when it is removed from its packaging or other storage means and before being donned by a user. As with glove 10, glove 20 includes a finger and hand portion 1, a cuff 2, a cuff fold 3 and a cuff rim 4. In its folded over state, at least part of the inside surface of cuff 2 is exposed as an "outer facing surface". Cuff fold 3 forms an opening for a user to insert a hand into glove 20. Glove 20 further includes a "detachable" tab or detachable "donning" tab 5, having a non-free end 6 and a free end 7, with non-free end 6 is coupled on the inside surface of cuff 2. In one embodiment, detachable tab 5 is coupled on the outer facing surface of cuff 2 in its folded over state. In one embodiment, detachable tab 5 is generally rigid. A user can pick up and manipulate sterile glove 20 by grasping only free end 7 of detachable tab 5 with a first hand. A second hand can then be inserted through the cuff fold opening.

In one embodiment, non-free end 6 is coupled at or near cuff fold 3, and free end 7 of detachable tab 5 projects from fold 3. This ensures that the opening in cuff fold 3 is adequately supported and does not unfold while the second hand is being inserted. Non-free end 6 in this embodiment may assist in forming or maintaining the opening. Subsequently, all or at least the touched part of free end 7 of detachable tab 5 can be detached after the second hand is inserted (and before the glove is used), leaving glove 20 securely on the second hand without any remaining part of the glove having been in contact with the user's first hand. In one embodiment, all of the detachable portion to tab 5 is coupled to the outer facing surface when the cuff is folded over at the fold.

In one embodiment, the size between cuff rim 4 and cuff fold 3, and the size of the outer facing surface are approximately the same as in typical prior art sterile gloves, such as glove 10 of FIG. 1. Although when donning glove 20 there is no contact between the user's first hand and any part of the glove, there is still a need to have a significant area of the inside surface near rim 3 to not come into contact with the skin of the second hand while it is being inserted. Locating at least a portion of non-free end 6 at or near fold 3 provides unexpected advantages in comparison to locating it at or near the rim at some distance away from the fold, since there will be a tendency for the cuff to unfold as a hand is being inserted and non-free end 6 can prevent this. In one embodiment, non-free end 6 is coupled at or near fold 3 to ensure the size of the outer facing surface during donning is maintained to be approximately the same size as in prior art gloves such as 10, and is at least not significantly smaller. In one embodiment the closest portion of non-free end 6 to cuff 3 is closer to cuff 3 than it is to cuff rim 4. In one embodiment, fold 3 is positioned such that no detachable part of free end 7 is on the inner facing surface (opposite of the outer facing surface) of the cuff when the cuff is folded.

In one embodiment, the outer facing surface forms an approximate plane and at least a portion of free end 7 of detachable tab 5 projects in a direction substantially perpendicular to the plane. In one embodiment, at least a portion of free end 7 of detachable tab 5 projects in a direction substantially radial to the longitudinal axis of glove 20 (the longitudinal axis being defined as running through the center of the cuff fold opening towards hand and finger portion 1). In one embodiment, free end 7 extends sufficiently away from the outer facing surface to minimize risks of a user's first hand coming into contact with any other part of glove 20, and to minimize the risk of the user's first hand coming into contact with any part of the user's second hand, or the arm or sleeve of the second hand, while the second hand is being inserted into the glove.

Figure 3:
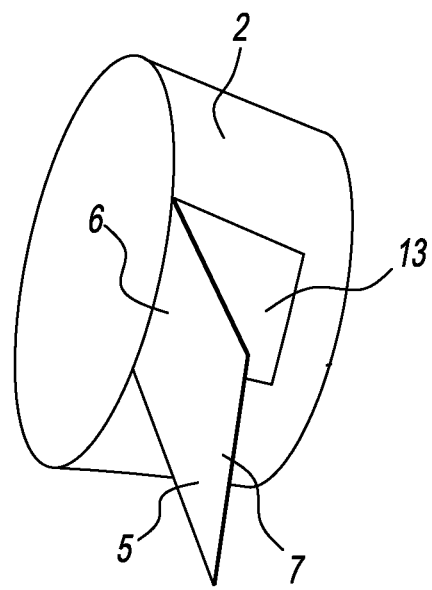
FIG. 3 is a perspective view of a detachable tab in accordance with another embodiment.

Non-free end 6 of tab 5 is detachably coupled to cuff 2. In one embodiment, non-free end 6 is generally rigid and helps to hold fold 3 in an open position. For example, as shown in FIG. 2, non-free end 6 may be approximately T-shaped, having arms 11, 12 that extend along fold 3. FIG. 3 is a perspective view of detachable tab 5 in accordance with another embodiment. In the embodiment of FIG. 3, detachable tab 5 is substantially L-shaped, with non-free end 6 having substantially rigid portion 13 that extends along the outer facing surface away from the cuff fold 3 towards rim 4, forming substantially a right angle with free end 7 that projects rigidly above the outer facing surface of cuff 2. Portion 13 therefore assists the user in securely holding the glove via free end 7, while minimizing the chances of contact between the first hand and the outer facing surface. In one embodiment, portion 13 is also detachably coupled to cuff rim 4 and can be used to unfold the cuff as it is removed. Embodiments are possible with angles other than right angles between portion 13 and free end 7.

In embodiments, free end 7 of detachable tab 5 extends sufficiently from glove 20 to be easily grasped by a user without touching any other part of the glove. Any object that can be suitably grasped can be used for detachable tab 5, including a tab, loop, appendage, handle, etc. (collectively referred to as a "tab"). In one embodiment, sterile glove 20 is made with elastomeric impermeable material, such as latex or other suitable material, to prevent contamination.

Figure 4:
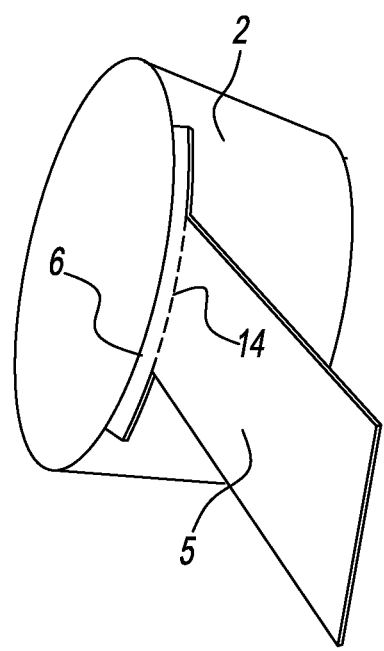
FIG. 4 is a perspective view of a detachable tab in accordance with another embodiment.

Detachable tab 5 can be located on cuff 2 by any known attachment mechanism that enables both a sufficiently strong attachment to allow glove 20 to be grasped firmly while donning and that also enables all, or at least the touched portion, of tab 5 to be subsequently detached. FIG. 4 is a perspective view of detachable tab 5 in accordance with another embodiment. In FIG. 4, tab 5 is secured to cuff 2 by an adhesive and includes, immediately adjacent to the glued area, perforations 14 that span all, or part of, the width of tab 5. Perforations 14 enable tab 5, when pulled in a suitable direction, to tear away from the adhered area. This embodiment leaves at least some portion of non-free end 6 of tab 5 still coupled to cuff 2 after the touched part is torn away. In one embodiment, fold 3 is positioned such that none of the detachable part of the tab is located on the inner facing part of the cuff when the cuff is folded. The remaining portion of non-free end 6 is located on the inside surface of cuff 2 when cuff 2 is fully unfolded and the glove is in use, and therefore the remaining portion will be entirely on the inside of the cuff, leaving nothing that will interfere with the use of the glove. In one embodiment all of the detachable portion is coupled to the outer facing surface when the cuff is folded over at the fold.

In another embodiment, the entire tab 5 is detached by using a suitable releasable adhesive or a releasable fastener, such as Velcro. In one embodiment, a directional releasable adhesive can be used, which holds firmly in place when pressure is applied in the direction of the longitudinal axis of the glove, but peels away easily when transverse pressure is applied. In one embodiment, tab 5 is attached to cuff 2 in a manner that insures that the user cannot apply too much force to glove 20 while donning it to minimize the risk of over stretching or tearing, thereby improving safety.

Tab 5 can be constructed of any suitable lightweight material, such as a plastic, that allows the glove to be securely held during donning and that can be easily be sterilized. Tab 5 can be of any size and shape that is convenient. Non-free end 6 of tab 5 can be of any size and shape that is convenient and can be rigid enough to hold fold 3 open while being donned. All of tab 5 can be made of a suitable rigid material. Generally rigid material results in one embodiment in tab 5 being sufficiently stiff or inflexible such that when a user is grasping free end 7 of tab 5, the tab does not bend or change shape under the tension introduced as a second hand is inserted into the glove. A tab less rigid than this would increase the risk of the user's first hand coming into contact with another part of the glove, or with some part of the user's second hand or arm during donning.

Figure 5:
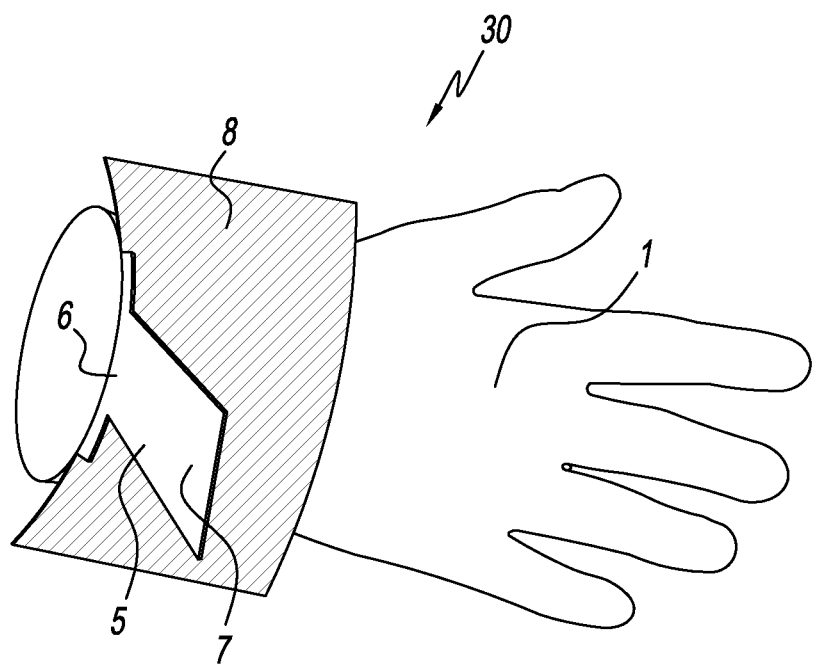
FIG. 5 is a perspective view of a sterile glove in accordance with another embodiment.

FIG. 5 is a perspective view of a sterile glove 30 in accordance with another embodiment. Glove 30 is similar to glove 20 of FIG. 2, but further includes a detachable shield 8 coupled to the glove and that covers at least a portion of the outer facing surface of cuff 2. In one embodiment, glove 30 is packaged in a sterile envelope (not shown) which when opened presents glove 30 to the user with its cuff folded over as shown in FIG. 5. In one embodiment at least a part of free end 7 of detachable tab 5 projects substantially perpendicularly from the outer facing surface of cuff 2. In one embodiment, at least a portion of shield 8 lies between free end 7 of detachable tab 5 and the outer facing surface of the cuff when the glove is folded and/or packaged. In one embodiment when the glove is packaged, the first detachable shield is between the detachable tab and the outer facing surface so that the free end of the detachable tab does not contact the outer facing surface. In one embodiment, shield 8 is coupled at or near the fold and extends in a direction towards the cuff rim 4. In one embodiment, shield 8 covers at least a portion of the outer facing surface from where free end 7 projects from the glove, extending in a direction towards cuff rim 4. In one embodiment, the size/distance on glove 30 between cuff rim 4 and cuff fold 3, and the size of the outer facing surface are approximately the same as in typical prior art sterile gloves, such as glove 10 of FIG. 1. In one embodiment, shield 8 covers the entire outer facing surface of the folded cuff that is on the same side of the glove as detachable tab 5. In one embodiment, the fold is positioned such that no detachable part of the tab or shield is located on the inner facing surface of the cuff when the cuff is folded.

When donning glove 30, a user can pick up and manipulate sterile glove 30 by grasping free end 7 of detachable tab 5 with a first hand. Detachable shield 8 ensures that there is no contact between the user's first hand and any other part of the glove other than the tab or the shield. A second hand can then be inserted through the cuff fold opening. Subsequently, all or at least the touched part of detachable tab 5 can be detached, and all or at least the touched part of detachable shield 8 can be detached. This leaves glove 30 securely on the second hand without any remaining surface having been in contact with the user's first hand. In one embodiment, shield 8 and tab 5 are coupled together so removing all or at least the touched part of detachable tab 5 also removes all or at least the touched portion of detachable shield 8. In one embodiment, shield 8 can also be detachably coupled to rim 4 of the glove cuff, such that it can be used to unfold the glove cuff as it is being detached. In one embodiment, at least all of the touched parts of the detachable tab and detachable shield are removed before the glove is used.

Detachable shield 8 can be any shape and size that is convenient, provided it is large enough to ensure that free end 7 of detachable tab 5 can be easily grasped without touching any part of the glove other than shield 8 and tab 5. In one embodiment, shield 8 is wider than free end 7 of detachable tab 5. In one embodiment, shield 8 is wider than non-free end 6 of detachable tab 5. In one embodiment, shield 8 is wider than the cuff. In one embodiment, shield 8 extends from the cuff fold towards the cuff rim at least a distance greater than the length of the free end of detachable tab. In one embodiment, shield 8 extends from the cuff fold to the cuff rim. In one embodiment, shield 8 extends from the cuff fold to beyond the cuff rim. In one embodiment, detachable shield 8 is coupled to the glove such that it covers at least a portion of the outer facing surface from where free end of detachable tab projects from the glove, extending in a direction towards the cuff rim. Detachable shield 8 can be made of any suitable lightweight material that can also be readily sterilized, such as a flexible plastic sheet. Detachable shield 8 can be coupled by using any suitable releasable adhesive or releasable fastening means. In one embodiment detachable shield 8 and detachable tab 5 can be formed as a single piece.

Figure 6:
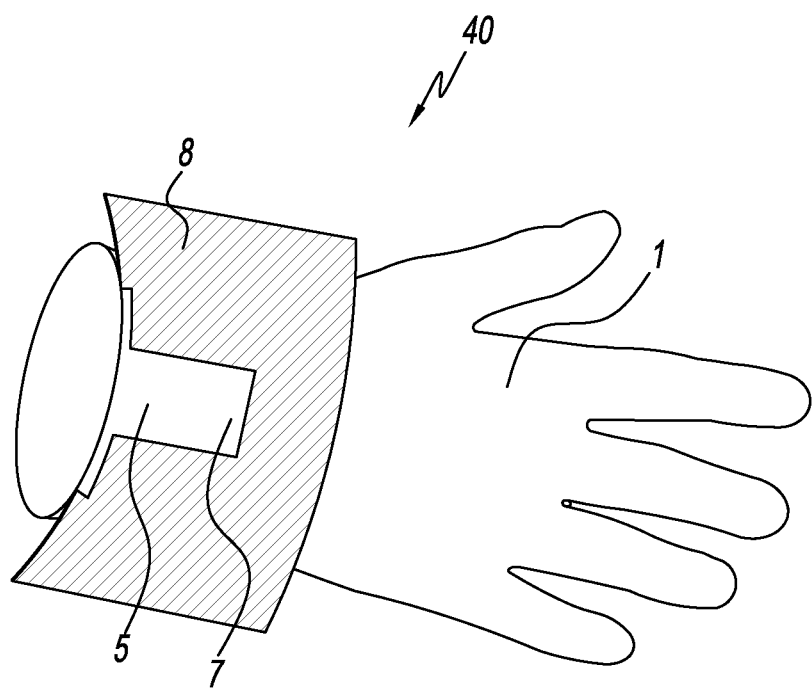
FIG. 6 is an perspective view of a sterile glove which can be packed flat in accordance with one embodiment.

FIG. 6 is a perspective view of a sterile glove 40 which can be packed flat in accordance with one embodiment. Glove 40 is similar to glove 30 of FIG. 5 except that free end 7 of detachable tab 5 is packaged flat against the outward side of shield 8 that is opposite to the side touching the outer facing surface of the cuff. In this embodiment, tab 5 is rigid and free end 7 rests within the boundaries of shield 8 by a sufficient margin, to ensure that free end 7 can be easily grasped without touching anything other than the outward side of shield 8. A user can grasp free end 7 of detachable tab 5 and lift it into a position where it projects substantially perpendicularly from the outer facing surface and shield 8. At this point, glove 40 can be donned in a similar manner as glove 30 of FIG. 5. In another embodiment, detachable tab 5 can be substantially L-shaped (as with tab 5 of FIG. 3) with a flexible section or hinge means between the two sections of the L-shape. This allows for the glove to be packaged flat. In one embodiment, the hinge means can be locked into a substantially perpendicular position to assist stability while inserting a hand. Embodiments are possible where the hinge means can be locked at angles other than perpendicular.

Figure 7:
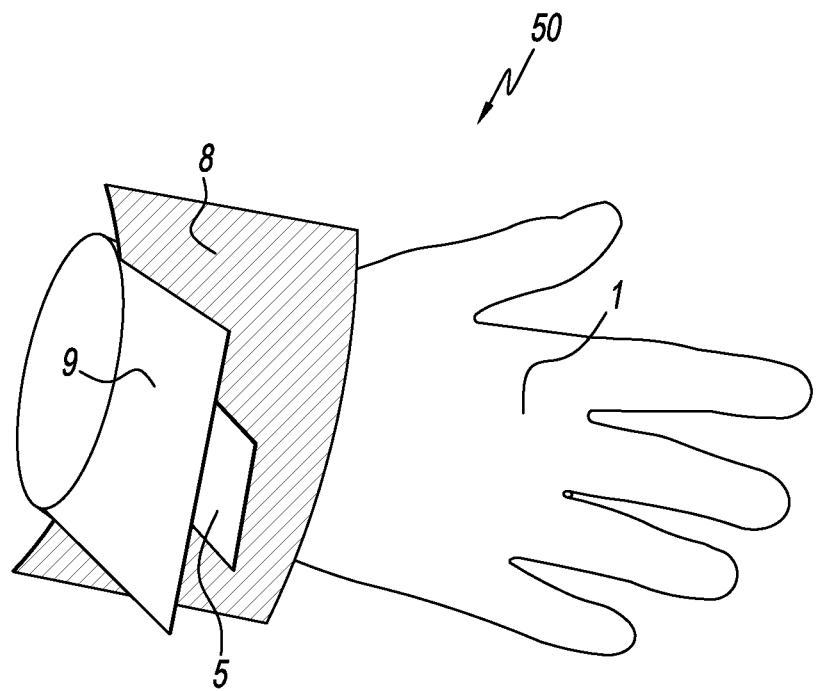
FIG. 7 is a perspective view of a sterile glove in accordance with one embodiment.

FIG. 7 is a perspective view of a sterile glove 50 in accordance with one embodiment. Glove 50 includes at least two detachable shields 8 and 9 coupled to glove and a detachable tab 5 located between shields 8 and 9. A user can use a first hand to grasp and manipulate glove 50 by the free end 7 of detachable tab 5, while inserting a second hand into the glove. Shields 8 and 9 ensure that there is no contact between the user's first hand and any wearable part of the glove or between the first hand and the skin of the second hand or any part of an arm or sleeve of the user's second hand. Once the glove is securely on the second hand, tab 5 and shields 8 and 9 can be detached. In one embodiment, tab 5 and one or both of shields 8 and 9 may be coupled together so they are easily detached together. In one embodiment, shield 8 is coupled at or near cuff rim 4 in such a manner that removing shield 8 also unfolds the folded over cuff. Shield 8 can be of any size, shape or material that is convenient and that can be readily sterilized and can be attached by similar means as used for shield 8 as described for glove 30. A variation on this embodiment is possible with only a shield 9 and a detachable tab 5.

Figure 8:
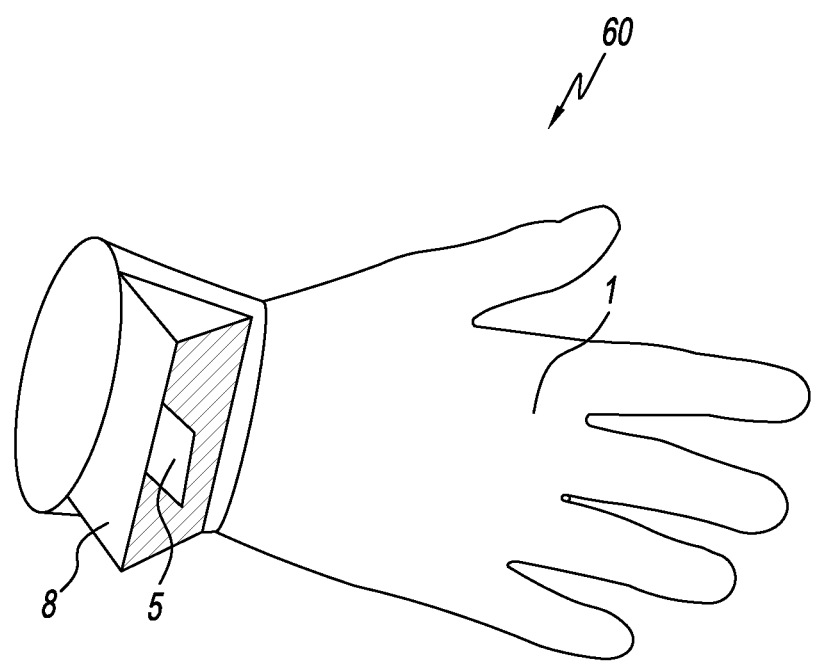
FIG. 8 is a perspective view of a sterile glove in accordance with one embodiment.

FIG. 8 is a perspective view of a sterile glove 60 in accordance with one embodiment. Glove 60 includes a detachable shield 8 that forms an enclosure around at least the free end of detachable tab 5. Completely enclosing free end 7 of tab 5 in this way provides additional protection against the risk of contact between a first hand used to grasp tab 5 and a second hand as it is inserted into glove 60. All other aspects of this embodiment are similar to the equivalent elements as described above for gloves 20, 30, 40 and 50.

Figure 9:
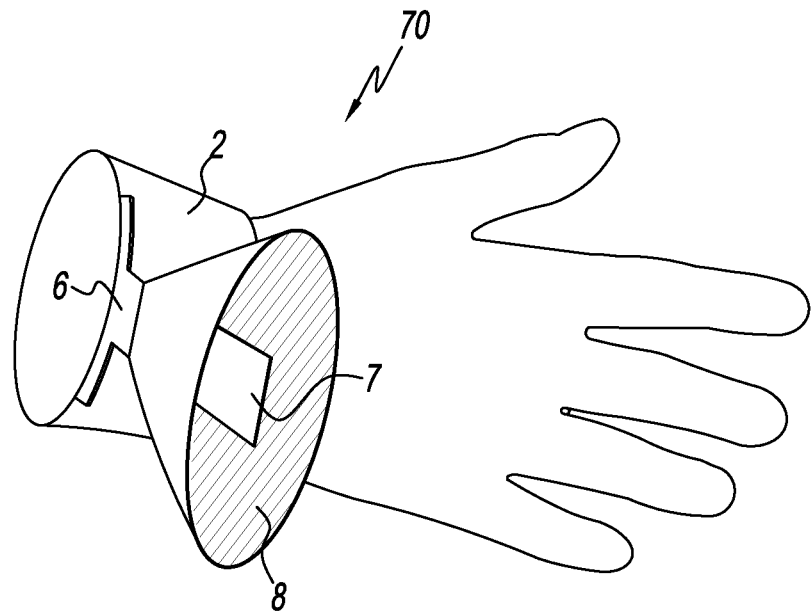
FIG. 9 is a perspective view of a sterile glove in accordance with one embodiment.

FIG. 9 is a perspective view of a sterile glove 70 in accordance with one embodiment. Glove 70 includes a detachable shield 8 that is coupled to the detachable tab and forms an enclosure around at least the free end of 7. Completely enclosing tab 5 in this way provides additional protection against the risk of contact between a first hand used to grasp tab 5 and a second hand as it is inserted into glove 60. All other aspects of this embodiment are similar to the equivalent elements as described above for gloves 20, 30, 40, 50 and 60.

Figure 10:
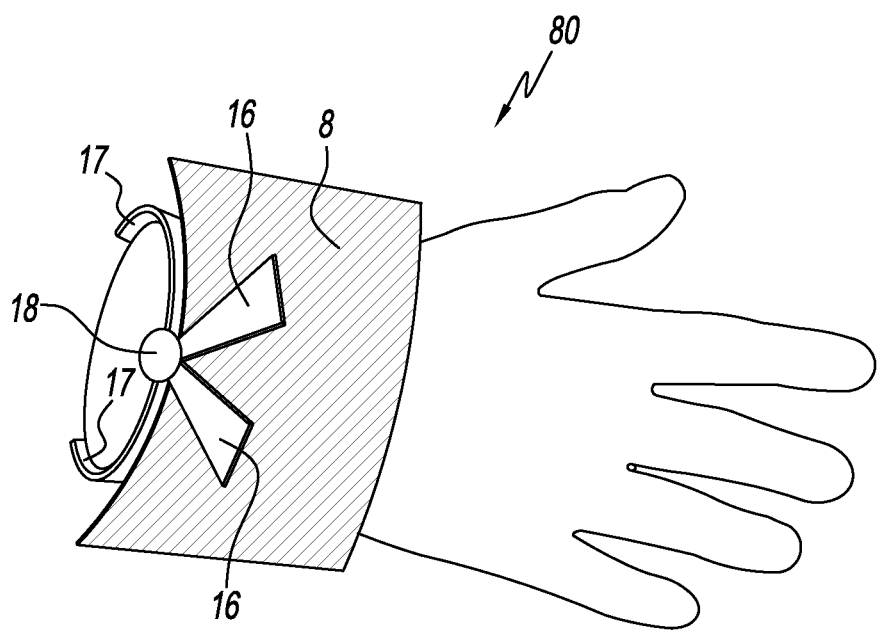
FIG. 10 is a perspective view of a sterile glove in accordance with one embodiment.

FIG. 10 is a perspective view of a sterile glove 80 in accordance with one embodiment. Glove 80 is similar to glove 30 except that detachable tab 5 is replaced by a detachable stretching mechanism 15. Stretching mechanism 15 includes a pair of handles 16, a pair of stretching arms 17 coupled at or near cuff fold 3, and a pivot 18. Handles 16 are coupled to stretching arms 17 though pivot 18. When handles 16 are in an opened position fold 3 is in a minimal or unstretched state. When handles 16 are pressed together towards a closed position, fold 3 is in a stretched state. Therefore, in a stretched state, stretching mechanism 15 increases the opening of glove 80 to allow a user to more easily insert a hand. Any object that can be suitably grasped can be used for handle 16, including a tab, loop, appendage, etc. (collectively referred to as a "handle"). In one embodiment, handles 16 are similar to the handles of conventional scissors or forceps. In one embodiment, glove 80 is packaged in a sterile envelope (not shown) which when opened presents glove 80 to the user in an unstretched state as shown in FIG. 10. The user can manipulate sterile glove 80 by grasping handles 16 between the user's thumb and forefinger of a first hand. Shield 8 prevents the user's first hand from coming into contact with any other part of the glove. Stretching mechanism 15 can then be actuated by pressing the forefinger and thumb towards each other, causing handles 16 to move to a closed position and arms 17 to open through pivot 18. A second hand can then be inserted more easily through the cuff fold opening in its stretched state. Subsequently, all or part of the stretching mechanism 15 can be detached, leaving glove 80 securely on the second hand without any remaining surface having been in contact with the user's first hand. Subsequently shield 8 can be detached. In one embodiment, only the handles 16 are detached, leaving arms 17 and pivot 18 on the inside of glove 80 when cuff 2 is unfolded. In one embodiment, handles 16 include a pre-weakened area adjacent to pivot 18, which separates when pressure is applied in a suitable direction. In another embodiment, handles 16, arms 17 and pivot 18 are all detached prior to the cuff 2 being unfolded. In one embodiment, pivot 18 decouples if pulled in a direction away from finger and hand portion 1 of glove 80, enabling handles 16 to be used to pull arms 17 away from the glove 80. In this embodiment, the adhesive used to couple arms 17 to cuff 2 releases when pulled in a particular suitable direction. In some embodiments, stretching mechanism 15 is packaged in an unstretched state. Other detachable stretching mechanisms can be used. In one embodiment, shield 8 is also detachably coupled to cuff rim 4 and can be used to unfold the cuff as it is removed. Sterile glove 80 can further include an additional detachable tab (not shown), coupled substantially at or near cuff rim 4 and adapted for unfolding the folded cuff after a hand has been inserted and before the glove is used.

Several embodiments are specifically illustrated and/or described herein. However, it will be appreciated that modifications and variations of the disclosed embodiments are covered by the above teachings and within the purview of the appended claims without departing from the spirit and intended scope of the invention.

What is claimed is:

1. A sterile glove comprising:
   a hand and finger portion;
   a cuff having an inside surface and an outside surface and a cuff rim, wherein the cuff is adapted to be folded over at a fold when the glove is packaged in a package, and wherein a portion of the inside surface of the cuff becomes an outer facing surface when folded over;
   a detachable tab coupled to the inside surface and comprising a free end and a non-free end; and
   a first detachable shield covering at least a portion of the outer facing surface when the cuff is folded over at the fold;
   wherein the first detachable shield is between the detachable tab and the outer facing surface.

2. The sterile glove of claim 1, wherein at least a rigid portion of the detachable tab is generally rigid and the non-free end is coupled substantially near the fold and is adapted to support an opening formed by the cuff.

3. The sterile glove of claim 1, wherein at least a rigid portion of the detachable tab is generally rigid and the non-free end is coupled substantially near the fold and is adapted is prevent the cuff from unfolding while a hand is being inserted into the glove.

4. The sterile glove of claim 1, wherein when the package is opened, the first detachable shield is between the detachable tab and the outer facing surface so that the free end of the detachable tab does not contact the outer facing surface.

5. The sterile glove of claim 1, wherein a detachable portion of the detachable tab is adapted to be removed after a hand has been inserted into the glove, and all of the detachable portion is coupled to the outer facing surface when the cuff is folded over at the fold.

6. The sterile glove of claim 1, further comprising a longitudinal axis, wherein the free end of the detachable tab is substantially rigid and extends approximately in a radial direction from the longitudinal axis.

7. The sterile glove of claim 1, wherein the outer facing surface comprises an approximate plane, and wherein the free end of the detachable tab is substantially rigid and extends in a direction approximately perpendicular from the plane.

8. The sterile glove of claim 1, further comprising a second detachable shield, wherein when the glove is packaged, the detachable tab is between the first detachable shield and the second detachable shield.

9. The sterile glove of claim 1, wherein the first detachable shield forms an enclosure around the free end of the detachable tab.

10. The sterile glove of claim 1, wherein the first detachable shield is detachably coupled to the cuff rim.

11. The sterile glove of claim 1, wherein the detachable tab comprises a stretching mechanism that comprises a pivot, a pair of handles, and a pair of arms, and wherein the handles are coupled to the arms through the pivot.

12. A method of packaging in a package a sterile glove that comprises a hand and finger portion, and a cuff having an inside surface and an outside surface and a cuff rim, the method comprising;
   folding the cuff at a fold so that at least a portion of the inside surface of the cuff becomes an outer facing surface when folded over;
   coupling a detachable tab on the inside surface, wherein the detachable tab comprises a free end and a non-free end; and
   coupling a first detachable shield that covers at least a portion of the outer facing surface when the cuff is folded over at the fold;
   wherein when the package is opened packaged, the first detachable shield is between the detachable tab and the outer facing surface.

13. The method of claim 12, wherein at least a rigid portion of the detachable tab is generally rigid and the non-free end is coupled substantially near the fold and is adapted to support an opening formed by the cuff.

14. The method of claim 12, wherein at least a rigid portion of the detachable tab is generally rigid and the non-free end is coupled substantially near the fold and is adapted is prevent the cuff from unfolding while a hand is being inserted into the glove.

15. The method of claim 12, wherein when the package is opened, the first detachable shield is between the detachable tab and the outer facing surface so that the free end of the detachable tab does not contact the outer facing surface.

16. The method of claim 12, wherein a detachable portion of the detachable tab is adapted to be removed after a hand has been inserted into the glove, and all of the detachable portion is coupled to the outer facing surface when the cuff is folded over at the fold.

17. The method of claim 12, further comprising a second detachable shield, wherein when the glove is packaged, the detachable tab is between the first detachable shield and the second detachable shield.

18. The method of claim 12, wherein the first detachable shield forms an enclosure around the free end of the detachable tab.

19. The method of claim 12, wherein the first detachable shield is detachably coupled to the cuff rim.

20. The method of claim 12, wherein the detachable tab comprises a stretching mechanism that comprises a pivot, a pair of handles, and a pair of arms, and wherein the handles are coupled to the arms through the pivot.

* * * * *